United States Patent [19]
Itoh

[11] Patent Number: 5,336,886
[45] Date of Patent: Aug. 9, 1994

[54] APPARATUS FOR MEASURING A DIFFRACTION PATTERN OF ELECTRON BEAMS HAVING ONLY ELASTIC SCATTERING ELECTRONS

[75] Inventor: Kazuhiko Itoh, Tokyo, Japan

[73] Assignee: Japan Aviation Electronics Industry Limited, Tokyo, Japan

[21] Appl. No.: 48,244

[22] Filed: Apr. 19, 1993

[30] Foreign Application Priority Data

Apr. 24, 1992 [JP] Japan ................................. 4-106754

[51] Int. Cl.⁵ ............................................. H01J 37/295
[52] U.S. Cl. .................................... 250/305; 250/310; 250/397
[58] Field of Search ........................ 250/305, 310, 397

[56] References Cited

U.S. PATENT DOCUMENTS

| | | | |
|---|---|---|---|
| 3,461,306 | 8/1969 | Stout et al. | 250/49.5 |
| 4,742,223 | 5/1988 | Kesmodel | 250/305 |
| 5,148,025 | 9/1992 | Ahn et al. | 250/305 |

FOREIGN PATENT DOCUMENTS 1467802 12/1966 France .

OTHER PUBLICATIONS

"High-Resolution Low-Energy Electron Diffractometer" by Wendelken et al; Rev. Sec. 29, Instr., vol. 47, No. 9, Sep. 1976, pp. 1069–1078.
"High Sensitivity Low-Energy Electron Diffractometer" by Jenson et al Rev. Sci. Instr., vol. 60, No. 9, Sep./1989, pp. 3065–3067.
"Scanning Electron Diffraction With Energy Analysis" by Denbigh et al, J. Sci. Instr., vol. 42, 1965, pp. 305–311.

Primary Examiner—Jack I. Berman
Attorney, Agent, or Firm—Pollock, Vande Sande and Priddy

[57] ABSTRACT

An electron beam emitted from an electron gun is applied to an object whose crystal structure is being examined in a vacuum, and electron beams diffracted by the object are introduced into an energy discriminator of an energy analyzer which discriminates an electron beam or beams having a predetermined energy. The thus discriminated electron beams is converted by an electron beam detector into an electric signal for measuring the diffracted electron beam intensity.

3 Claims, 4 Drawing Sheets

APPARATUS FOR MEASURING A DIFFRACTION PATTERN OF ELECTRON BEAMS HAVING ONLY ELASTIC SCATTERING ELECTRONS

BACKGROUND OF THE INVENTION

The present invention relates to an electron beam diffraction measuring apparatus which applies an electron beam to a measuring object in a vacuum and examines its crystal structure on the basis of the intensity distribution of the electron beam diffracted by the measuring object. More particularly, the invention pertains to an electron beam diffraction measuring apparatus for scrutinizing the crystal structure of the measuring object by removing inelastic scattering. components of the diffracted electron beam.

FIG. 1 is a diagrammatic showing of a conventional electron beam diffraction measuring apparatus. The measuring apparatus in its entirety is placed in a vacuum. An electron beam 2 emitted from an electron gun 1 strikes on a measuring object 3 on a specimen table 20 and is scattered. At this time, the intensity distribution of scattered electrons is dependent on the energy of the electron beam 2 and the crystal structure of the measuring object 3—this phenomenon is called diffraction. On a fluorescent screen 4 disposed in the direction of diffracted electron beams 5 a pattern appears in accordance with the intensity distribution of the diffracted electron beams which corresponds to the crystal structure of the measuring object 3 (see FIG. 3, for instance). This pattern can be used to examine the crystal structure of the measuring object 3.

FIG. 2 is a schematic representation of another prior art example of electron beam diffraction measuring apparatus, which directly measures the intensity distribution of the diffracted electron beams 5 by means of an electron beam detector 6 instead of using the fluorescent screen 4 in FIG. 1. The intensity distribution of the diffracted electron beams 5 can be obtained by measuring the electron beam intensity while at the same time moving the electron beam detector 6 in a direction of a radius vector the rotating center of which is at the point of diffraction P on the specimen 3 by means of a driver not shown (i.e. turning the detector 6 around the point of diffraction P over an arcuate distance covering all the diffracted electron beams 5). FIG. 3 is a graph showing an example of the diffracted electron beam intensity distribution measured by the above method. The diffracted electron beam intensity distribution has maximal values in directions of plural diffraction angles α which are determined by conditions of diffraction, that is, the lattice plane and lattice constant of the measuring object 3, the angle of incidence θ of the electron beam 2 to the measuring object 3 and the energy of the electron beam 2 (an electron acceleration voltage eV or the wavelength of the electron beam 2). In this instance, the diffracted electron beam intensity does not become zero either at places other than those of the diffraction angles θ where the diffracted electron beam intensity has maximal values. This is because of the presence of inelastic scattering or multiple scattering components which are usually regarded as background components. When the measuring object is a material close to a perfect crystal, a diffracted electron beam intensity distribution is obtained which has a relatively low background level and a plurality of definite maximal values as shown in FIG. 3.

In the case where the measuring object is a material close to an amorphous material, a diffracted electron beam intensity distribution such as depicted by a solid line in FIG. 4 is obtained. In this case, the measuring object does not have many crystalline portions that satisfy the conditions of diffraction and the electron beams are mostly scattered by amorphous portions of the measuring object in unspecified directions; consequently, maximal values in the diffracted electron beam distribution are small and their peaks are broad. That is, the ratio of the inelastic or multiple scattering components, i.e. the above-mentioned background components, to elastic scattering components increases, and hence no sharp peaks appear in the diffracted electron beam intensity distribution. The broken line in FIG. 4 indicates the background components.

As described above, according to the prior art, when the measuring object has a crystal structure that is close to an amorphous structure, the ratio of the background components in the diffracted electron beam intensity distribution increases, and consequently, maximal values of the diffracted electron beam intensity distribution—a clue to clarification of the crystal structure—become indefinite. Hence it is difficult, in the prior art, to analyze the crystal structures of such materials.

SUMMARY OF THE INVENTION

It is therefore an object of the present invention to provide an electron beam diffraction measuring apparatus which is capable of performing a precise analysis of the crystal structures of materials close to amorphous materials by eliminating the inelastic scattering component forming one factor of the background component of the diffracted electron beam intensity distribution in a step of measuring electron beam intensity, thereby decreasing the background component and making manifest the maximal values of the diffracted electron beam intensity distribution and their peaks.

In the electron beam diffraction measuring apparatus according to the present invention, which is of the type that applies an electron beam to a measuring object in a vacuum and detects electron beams diffracted by the measuring object, a discriminator is provided which discriminates energies of diffracted electron beams and detects only an electron beam of a predetermined energy.

Thus, in the electron beam diffraction measuring apparatus according to the present invention the inelastic scattering component, which forms part of the background component, can be eliminated by means of the discriminator which detects only the electron beam or beams having a predetermined energy among a plurality of electron beams diffracted by the object to be measured.

The energy of elastic scattering electrons is equal to the energy of electrons in an electron beam incident on the object being measured, but the energy of inelastic scattering electrons is lower than the energy of the incident electron beam because of an energy loss that is caused during the scattering. Hence it is possible to eliminate the inelastic scattering component by discriminating only (elastic scattering) electrons of an energy equal to that of an electron beam incident on an object to be measured through use of an electron beam energy discriminator.

DESCRIPTION OF THE PREFERRED EMBODIMENT

Figure 1:
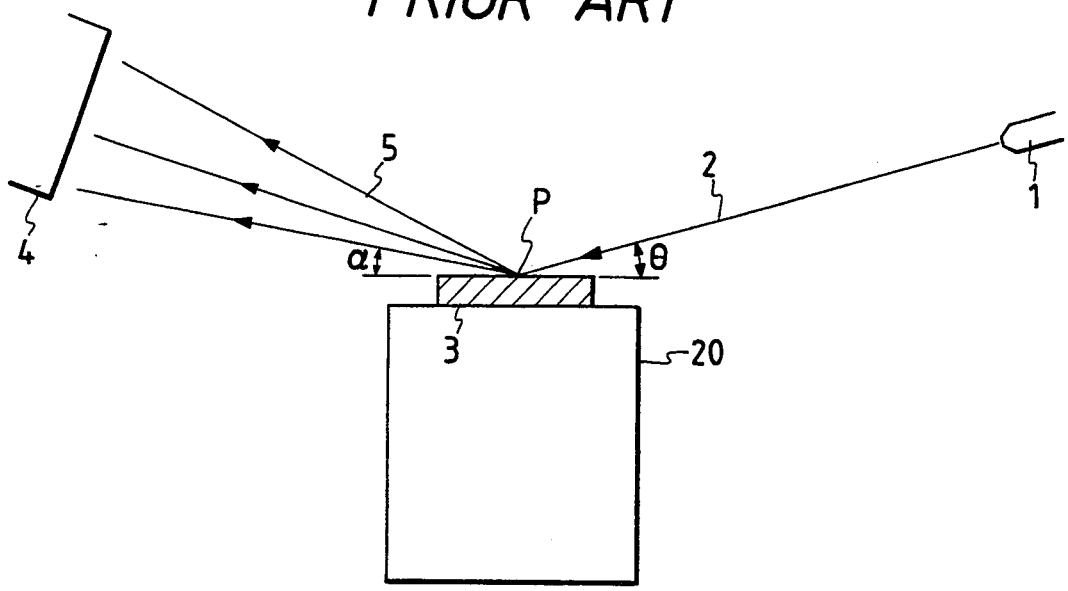
FIG. 1 is a schematic diagram of a conventional electron beam diffraction measuring apparatus.
Figure 2:
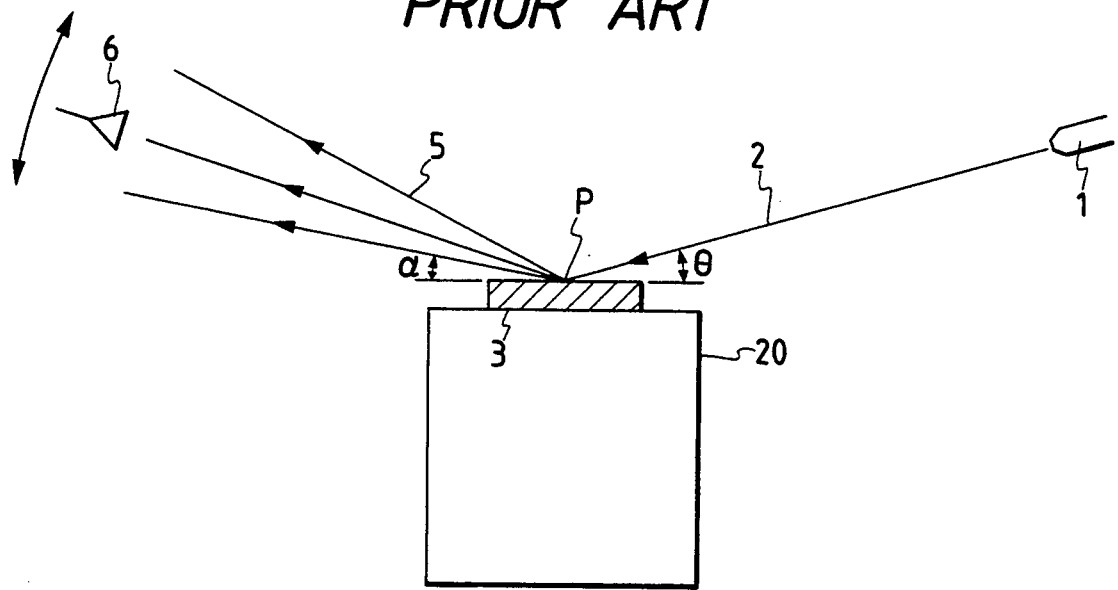
FIG. 2 is a schematic diagram of another conventional electron beam diffraction measuring apparatus.
Figure 3:
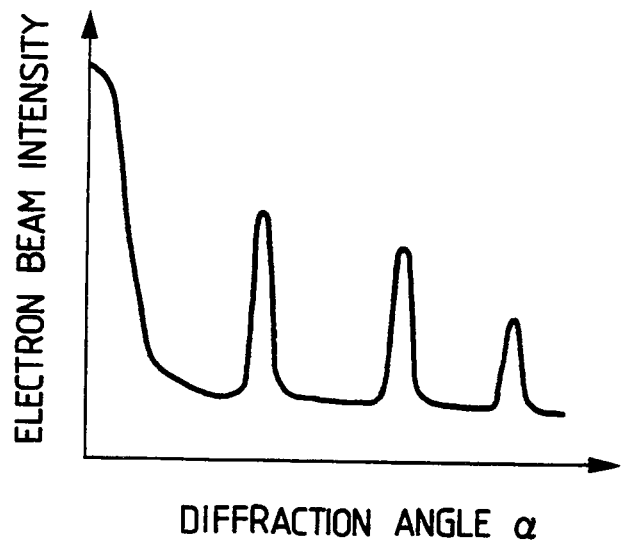
FIG. 3 is a graph showing an example of the diffracted electron beam intensity distribution obtained when the measuring object was crystalline.
Figure 4:
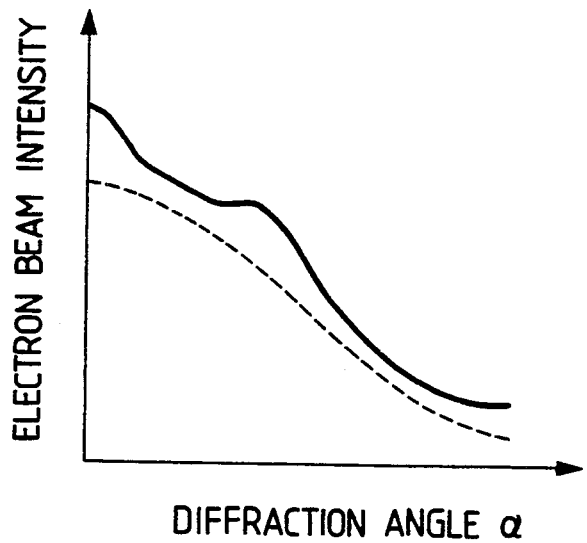
FIG. 4 is a graph showing the diffracted electron beam intensity distribution obtained when the measuring object was amorphous.
Figure 5:
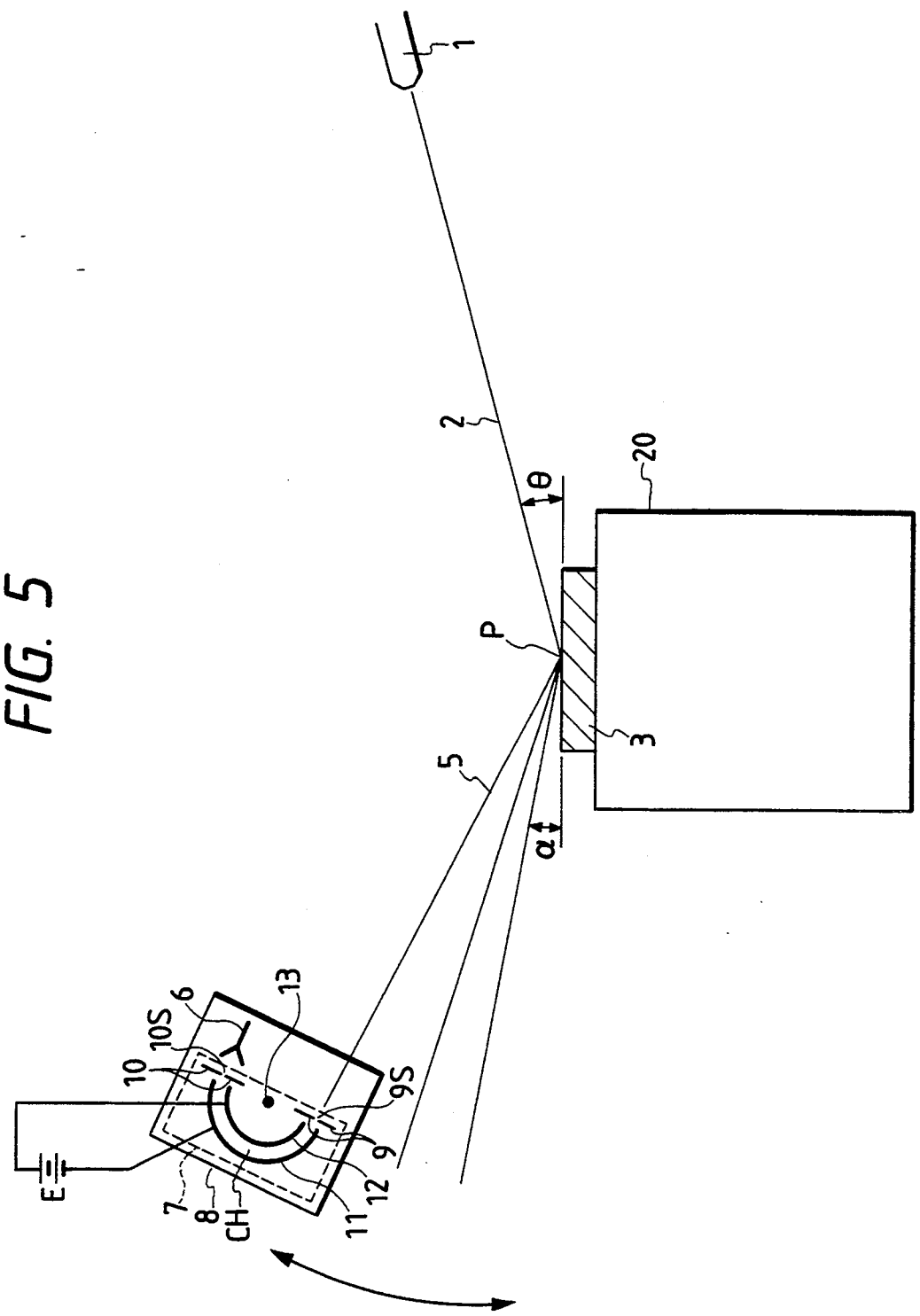
FIG. 5 is a diagram schematically illustrating an electron beam diffraction measuring apparatus in accordance with the present invention.
Figure 6:
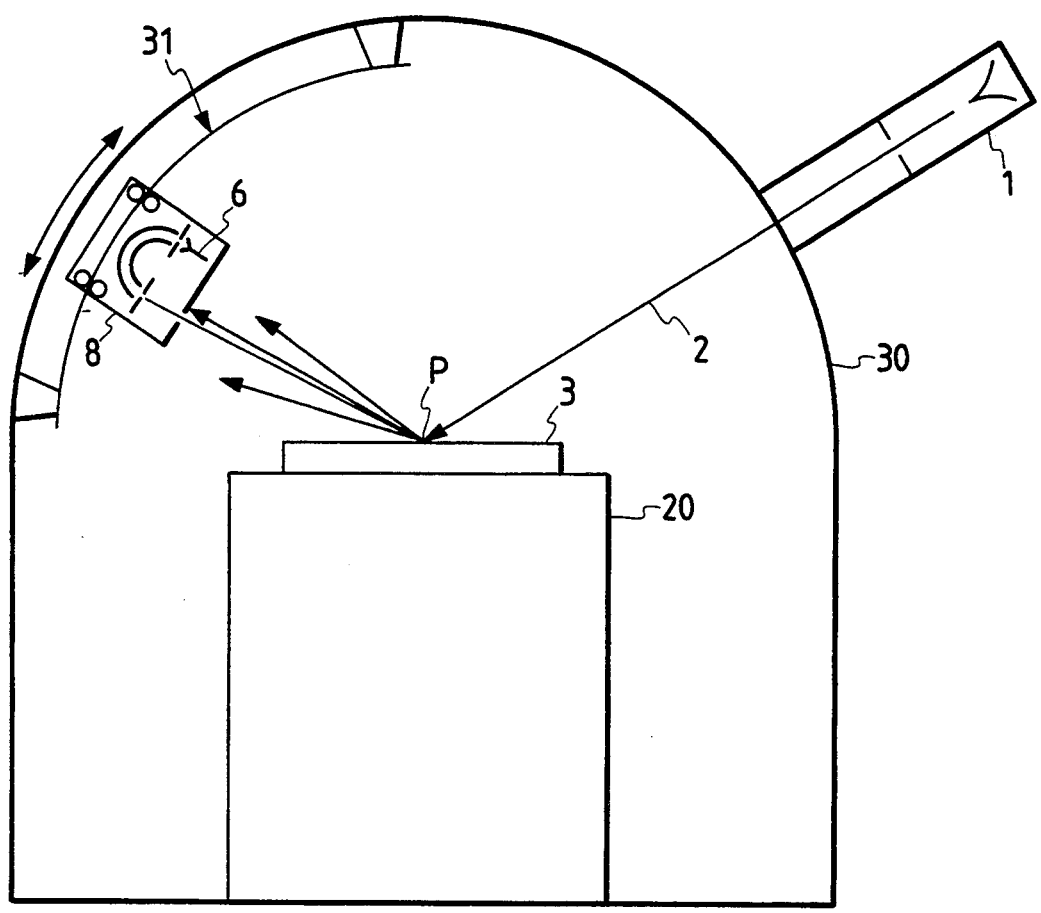
FIG. 6 is a schematic diagram showing the apparatus of FIG. 5 disposed in a vacuum vessel.

A description will be given, with reference to FIGS. 5 to 7, of an embodiment of the present invention. FIG. 5 illustrates an electron beam diffraction measuring apparatus according to the present invention. The entire apparatus is disposed in a vacuum. The electron beam 2 emitted from the electron gun 1 strikes on the measuring object 3 and is thereby diffracted. The diffracted electron beams 5 are received by an energy discriminator 7 of an energy analyzer 8, wherein only the electron beam or beams having a predetermined energy, that is, having substantially the same energy as that of the incident electron beam 2 on the object 3 among the diffracted electron beams 5, is discriminated. The electron beam or beams thus discriminated is detected by the electron beam detector 6.

The energy analyzer 8 comprises, for example, the electron beam detector 6 and the energy discriminator 7. The energy discriminator 7 is composed of an outer semi-cylindrical electrode 11 and an inner semi-cylindrical electrode 12 disposed several centimeters apart concentrically about an axis 13 to form a semi-circular channel CH, and slit plates 9 and 10 are placed at opposite open ends of the channel CH to block them and to provide an inlet slit 9S and an outlet slit 10S extending across the ends of the channel CH centrally thereof in parallel with the axis 13, respectively. The electron beam detector 6 is disposed opposite the outlet slit 10S. A fixed voltage is applied from a voltage source E across the inner semi-cylindrical electrode 12 held positive and the outer semi-cylindrical electrode 11 held negative, by which an electric field spreading out radially about the axis 13 is formed in the channel CH of the energy discriminator 7.

Electrons of the diffracted electron beams 5 are introduced into the channel CH of the energy discriminator 7 in its tangential direction through the inlet slit 9S. Since the electrons are subject to a force toward the axis 13 by the radial electric field in the channel CH, they perform a circular motion. The radius of this circular motion is dependent on the kinetic energy of the electrons and the intensity of the electric field applied to the semi-cylindrical electrodes 11 and 12, and consequently, only those electrons of a predetermined energy which perform the circular motion with a radius equal to the mean radius of the channel CH are emitted through the outlet slit 10S. When the kinetic energy of the electrons entering the electric field is smaller than the preset energy, the electrons are absorbed by the inner semi-cylindrical electrode 12, whereas electrons of a kinetic energy greater than the preset value are first bounced back by the outer semi-cylindrical electrode 11 and then absorbed by the inner semi-cylindrical electrode 12. Thus, only the electrons of a preset energy are discriminated and emitted through the outlet slit 10S.

The electrons thus emitted from the outlet slit 10S are introduced into the electron beam detector 6 such as an electron multiplier, wherein they are detected as an electric signal. The energy analyzer 8, which is made up of the energy discriminator 7 and the electron beam detector 6, is movably mounted on an arc-shaped or arcuate guide rail 31 fixed on the inner wall of the vacuum vessel 30 as shown in FIG. 6 and is moved, during the measuring of the intensities of the diffracted electron beams, by drive means (not shown) on the rail 31 in a direction of a radius vector the center of rotation of which is at the diffraction point P on the measuring object 3 (that is, the energy analyzer 8 is caused to move along a partial circular path around the point of diffraction P over an arcuate distance that covers all the diffracted electron beams). During the movement of the energy analyzer 8 a diffracted electron beam intensity distribution such as is depicted in FIG. 7 is derived from the output of the electron beam detector 6.

Figure 7:
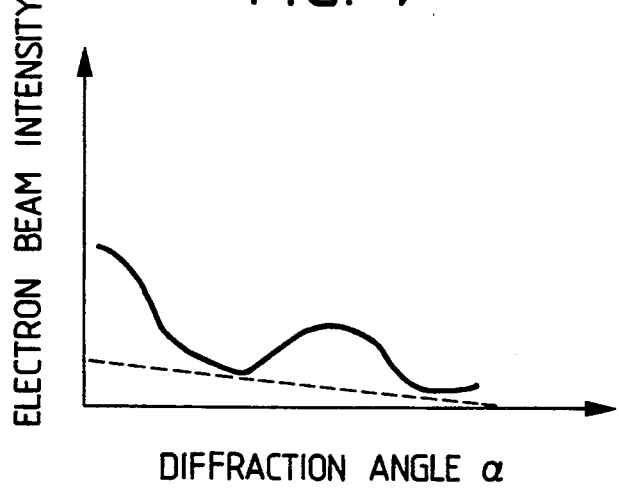
FIG. 7 is a graph showing an example of the diffracted electron beam intensity distribution obtained with the electron beam diffraction measuring apparatus according to the present invention when the measuring object was amorphous.

FIG. 7 shows an example of the diffracted electron beam intensity distribution measured when a measuring object having a crystal structure close to an amorphous structure is irradiated with an electron beam through use of the electron beam diffraction measuring apparatus according to the present invention. In this example, the electric field intensity in the energy discriminator 7 is set so that only diffracted electrons whose energy is equal to that of electrons in the beam 2 incident on the object 3 are discriminated, and inelastic scattering components of low energies are eliminated from the background components. Hence maximal values of the diffracted electron beam intensity distribution and their peaks are made manifest, permitting an easy analysis of the crystal structure of the measuring object which is close to an amorphous structure. The broken line in FIG. 7 indicates the background components.

While the above described embodiment employs, as the discriminator 7, an electric field type discriminator, it is also possible to use a magnetic field type energy discriminator. In such a discriminator diffracted electron beams are introduced through the inlet slit 9S into a uniform magnetic field formed between two pole faces parallel with the plane formed by rotation of the radius vector of the energy analyzer 8, instead of using the two semi-cylindrical electrodes 11 and 12, electrons entered into the magnetic field are allowed to perform a circular motion with a radius corresponding to their energy, and an electron beam or beams having a preset energy is emitted through the outlet slit 10S. Also it is possible to mount the energy analyzer 8 on an arm which turns about an axis passing through the diffraction point P, though not shown, instead of moving the analyzer 8 along the fixed arc-shaped guide rail 31 shown in FIG. 6.

As described above, the electron beam diffraction measuring apparatus of the present invention is provided with an energy discriminator which detects only an electron beam or beams having a preset energy, among plural electron beams diffracted by an object to be measured that has been irradiated in a vacuum with an electron beam having the preset energy, and therefore, inelastic scattering components forming part of background components of the diffracted electron beam intensity distribution can be eliminated. Hence, the invention makes it easier to analyze the crystal structure of a measuring object which is close to an amorphous structure.

It will be apparent that many modifications and variations may be effected without departing from the scope of the novel concepts of the present invention.

What is claimed is:

1. An electron beam diffraction measuring apparatus comprising:
    means for positioning an object to be measured at a predetermined location in a vacuum;
    an electron beam source for irradiating a portion of said object with an electron beam having a preset energy;
    energy discriminator means on which electron beams diffracted by said object are incident;
    drive means for moving said energy discriminator means around said portion of said object being irradiated by said electron beam from said electron beam source;
    said moving energy discriminator means being operative to emit therefrom only a beam of electrons having said preset energy among the electron beams that have been diffracted by said object and that are incident with substantially no loss of energy on said energy discriminator means; and
    electron beam detector means responsive to the beam of electrons having said preset energy emitted from said moving energy discriminator means for detecting a diffraction pattern of the energy discriminated electron beams diffracted by said object.

2. The apparatus of claim 1, wherein said energy discriminator means includes inlet and outlet slit means spaced apart a predetermined distance along an arcuate path defined by a radius vector of said diffracted electron beams, and field generating means for forming a field in a space between said inlet and outlet slit means to cause each electron entering said field through said inlet slit means to move along a circular path in said space with a radius that depends on the energy of said electron, said outlet slit means being so positioned relative to the radius of the circular path motion effected by electrons having said preset energy that only a beam of electrons having said preset energy is emitted through said outlet slit means into said electron beam detector means.

3. The apparatus according to claim 1, wherein said energy discriminator means includes inner and outer spaced-apart semi-cylindrical electrodes disposed concentrically to form a semi-circular channel therebetween, means for applying a voltage across said electrodes to cause said inner electrode to be higher in potential than said outer electrode, first and second slit plates disposed at opposite ends of said semi-circular channel to substantially block said opposite ends, each of said first and second slit plates having a slit therein formed in parallel with the axle of concentricity of said inner and outer semi-cylindrical electrodes, said diffracted electron beams being introduced into said channel through said slit of said first slit plate, and said beam of electrons having said preset energy being emitted from said channel to said electron beam detector means through said slit of said second slit plate.

* * * * *